(12) United States Patent
Gao et al.

(10) Patent No.: US 9,035,081 B2
(45) Date of Patent: May 19, 2015

(54) SYNTHESIS OF PHOSPHINIMIDE COORDINATION COMPOUNDS

(71) Applicant: NOVA Chemicals (International) S.A., Fribourg (CH)

(72) Inventors: Xiaoliang Gao, Calgary (CA); Zhiwei He, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 14/287,552

(22) Filed: May 27, 2014

(65) Prior Publication Data

US 2015/0005524 A1   Jan. 1, 2015

(30) Foreign Application Priority Data

Jun. 27, 2013 (CA) .................................. 2820501

(51) Int. Cl.
*C07F 9/28* (2006.01)
*C07F 7/28* (2006.01)

(52) U.S. Cl.
CPC ........................................ *C07F 7/28* (2013.01)

(58) Field of Classification Search
CPC ..................................................... C07F 9/5355
USPC ......................................................... 556/23
See application file for complete search history.

(56) References Cited

U.S. PATENT DOCUMENTS

| | | | |
|---|---|---|---|
| 6,355,744 B1 * | 3/2002 | von Haken Spence et al. ............................. | 526/127 |
| 2006/0122054 A1 | 6/2006 | Hoang et al. | |
| 2006/0247438 A1 * | 11/2006 | Ijpeij et al. ........................ | 546/2 |

FOREIGN PATENT DOCUMENTS

| CA | 2780508 A1 | 12/2013 |
|---|---|---|
| CA | 2798855 A1 | 12/2013 |

OTHER PUBLICATIONS

Courtenay, Silke; ONG, Christopher M. and Stephan, Douglas W.; Phosphinimido Complexes of Silicon, Tin, and Germanium; American Chemical Society, Organometallics 2003, 22, Publication on Web Jan. 18, 2003, pp. 818-825.

Pangborn, Amy B.; Giardello, Michael A.; Grubbs, Robert H; Rosen, Robert K. and Timmers, Francis J.; Safe and Convenient Procedure for Solvent Purification; American Chemical Society, Organometallics 1996, 15, pp. 1518-1520.

* cited by examiner

*Primary Examiner* — Porfirio Nazario Gonzalez
(74) *Attorney, Agent, or Firm* — Julie L. Heinrich

(57) ABSTRACT

Methods to make $R^1_3P\!\!=\!\!N\!\!-\!\!TiCl_3$ and $(1\text{-}R^2\text{-Indenyl})Ti(N\!\!=\!\!PR^1_3)Cl_2$, where $R^1$ is independently selected from $C_{1\text{-}30}$ hydrocarbyl radical which is unsubstituted or further substituted by one or more halogen atom, a $C_{1\text{-}8}$ alkoxy radical, a $C_{6\text{-}10}$ aryl radical, a $C_{6\text{-}10}$ aryloxy radical, an amido radical, a silyl radical, and a germanyl radical; P is phosphorus; N is nitrogen (and bonds to the metal M); $R^2$ is a substituted or unsubstituted alkyl group, a substituted or an unsubstituted aryl group, or a substituted or unsubstituted benzyl group, wherein substituents for the alkyl, aryl or benzyl group are selected from alkyl, aryl, alkoxy, aryloxy, alkylaryl, arylalkyl and halide substituents. The method to make $R^1_3P\!\!=\!\!N\!\!-\!\!TiCl_3$ combines a titanium species $TiCl_3(OR)$ where R is an alkyl or aromatic group, with a trimethylsilyl phosphinimide compound $R^1_3P\!\!=\!\!N\!\!-\!\!SiMe_3$ in the presence of solvent, to give the titanium complex $R^1_3P\!\!=\!\!N\!\!-\!\!TiCl_3$. The method to make $(1\text{-}R^2\text{-Indenyl})Ti(N\!\!=\!\!PR^1_3)Cl_2$ consists of deprotonating 1-$R^2$-indene with an appropriate base, followed by reaction with $R^1_3P\!\!=\!\!N\!\!-\!\!TiCl_3$.

35 Claims, No Drawings

SYNTHESIS OF PHOSPHINIMIDE COORDINATION COMPOUNDS

FIELD

Provided is an improved synthetic route to the titanium complexes $R^1_3P\!=\!N\!-\!TiCl_3$ and $(1\text{-}R^2\text{-Indenyl})Ti(N\!=\!PR^1_3)Cl_2$, where $R^1$ is independently selected from a $C_{1\text{-}30}$ hydrocarbyl radical which is unsubstituted or further substituted by one or more halogen atom, a $C_{1\text{-}8}$ alkoxy radical, a $C_{6\text{-}10}$ aryl radical, a $C_{6\text{-}10}$ aryloxy radical, an amido radical, a silyl radical, and a germanyl radical. An $R^2$ group is a substituted or unsubstituted alkyl group, a substituted or an unsubstituted aryl group, or a substituted or unsubstituted benzyl group.

BACKGROUND

The identification of new and improved synthetic methods for making catalysts and catalyst precursors for use in highly active polymerization catalysis is of importance to the polymer industry.

The known catalyst $(1\text{-}C_6F_5CH_2\text{-Indenyl})Ti(N\!=\!P(t\text{-}Bu)_3)Cl_2$ has been successfully employed as an active olefin polymerization catalyst (see CA Patent Application Nos. 2,780,508 and 2,798,855). Previous methods for making catalysts of this general type, e.g., $(1\text{-}R^2\text{-Indenyl})Ti(N\!=\!PR^1_3)Cl_2$ where $R^1$ and $R^2$ are unsubstituted or substituted hydrocarbyl type groups (see, for example, U.S. Patent Application No. 2006/0122054 and CA Patent Application Nos. 2,780,508 and 2,798,855) as well as methods for making important precursor molecules, although effective, are difficult to scale up to a commercially significant scale.

SUMMARY

Provided is a method for making $R^1_3P\!=\!N\!-\!TiCl_3$, said method comprising combining $TiCl_3(OR)$ with an approximately equimolar amount of $R^1_3P\!=\!N\!-\!SiMe_3$ in the presence of solvent, to give as reaction products the $R^1_3P\!=\!N\!-\!TiCl_3$ and $RO\!-\!SiMe_3$ wherein $R^1$ is independently selected from the group consisting of a $C_{1\text{-}30}$ hydrocarbyl radical which is unsubstituted or further substituted by one or more halogen atoms, a $C_{1\text{-}8}$ alkoxy radical, a $C_{6\text{-}10}$ aryl radical, a $C_{6\text{-}10}$ aryloxy radical, an amido radical, a silyl radical, and a germanyl radical; and wherein R is a primary, secondary or tertiary alkyl group or an aromatic group.

Provided is a method for making $(1\text{-}R^2\text{-Indenyl})Ti(N\!=\!PR^1_3)Cl_2$ comprising the following steps:
i) combining $TiCl_3(OR)$ with an approximately equimolar amount of $R^1_3P\!=\!N\!-\!SiMe_3$ to give $R^1_3P\!=\!N\!-\!TiCl_3$;
ii) combining a 1-substituted indene $1\text{-}R^2\!-\!C_9H_7$ with an approximately equimolar amount of lithium di-isopropylamide to give a 1-substituted indenide $1\text{-}R^2\!-\!C_9H_6$ anion;
iii) combining the 1-substituted indenide $1\text{-}R^2\!-\!C_9H_6$ anion with the $R^1_3P\!=\!N\!-\!TiCl_3$ to give $(1\text{-}R^2\text{-Indenyl})Ti(N\!=\!PR^1_3)Cl_2$; wherein $R^1$ is independently selected from a $C_{1\text{-}30}$ hydrocarbyl radical which is unsubstituted or further substituted by one or more halogen atoms, a $C_{1\text{-}8}$ alkoxy radical, a $C_{6\text{-}10}$ aryl radical, a $C_{6\text{-}10}$ aryloxy radical, an amido radical, a silyl radical, and a germanyl radical; R is a primary, secondary or tertiary alkyl group or an aromatic group; and $R^2$ is a substituted or unsubstituted alkyl group, a substituted or unsubstituted aryl group, or a substituted or an unsubstituted benzyl group.

DETAILED DESCRIPTION

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the desired properties, which the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

Provided are new methods for synthesizing active polymerization catalysts as well as catalyst precursor compounds. The new methods eliminate the need for low temperature steps and avoid difficult and time consuming filtration steps in order to obtain acceptable yields at large scales (e.g., at least about 400 mmol).

An indenyl ligand, "indenyl" or "Ind" as defined herein will have framework carbon atoms with the numbering scheme provided below, so the location of a substituent can be readily identified.

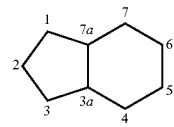

An indenyl ligand is an anionic species and prior to coordination to a suitable metal center will typically exist as an indenide metal salt: for example a substituted or unsubstituted indenide salt of lithium.

In some embodiments, a phosphinimide ligand $R^1_3P\!=\!N\!-\!$ is substituted on the phosphorus atom (P) with three $R^1$ groups, which are independently selected from a $C_{1-30}$ hydrocarbyl radical which is unsubstituted or further substituted by one or more halogen atoms, a $C_{1-8}$ alkoxy radical, a $C_{6-10}$ aryl radical, a $C_{6-10}$ aryloxy radical, an amido radical, a silyl radical, and a germanyl radical. A phosphinimide ligand is anionic and coordinates to a suitable metal center (for example, Ti, Zr, Hf) through the nitrogen atom (N).

As used herein "hydrocarbyl" or "hydrocarbyl radical" refers to an organic compound consisting entirely of hydrogen and carbon from which one hydrogen atom has been removed allowing for a bond or link to form with another compound, chemical group or atom. Aromatic hydrocarbons (arenes), alkanes, alkenes, cycloalkanes and alkyne-based compounds are different types of hydrocarbons that, when one hydrogen is removed, form radicals including aryl, alkyl, alkenyl, cycloalkyl, and alkynyl. Hydrocarbyl radicals may be optionally substituted with additional atoms, functional groups or radicals as described herein.

In some embodiments, a titanium compound $R^1_3P$=$NTiCl_3$ which has a phosphinimide ligand in its coordination sphere is made using a new synthetic route. The new synthetic method involves the use of a trichlorotitanium hydrocarbyloxide $TiCl_3OR$ which, when reacted with a trimethylsilyl phosphinimide $R^1_3P$=$N$—$SiMe_3$ species, gives the desired product $R^1_3P$=$N$—$TiCl_3$ in high yield at large scale. The fact that this reaction works well at large scale (e.g., at least about 400 mmol scales) allows facile production of active phosphinimide ligated olefin polymerization catalysts at a commercially relevant scale Step 1: Preparation of $TiCl_3(OR)$, Option A:

An alcohol ROH is combined with titanium tetrachloride ($TiCl_4$) in the presence of a solvent, such as a hydrocarbon solvent, in approximately equimolar amounts. Note that an alcohol ROH can be pre-dried with a suitable drying agent, such as, for example, NaOEt followed by distillation. In an embodiment, an aromatic solvent (e.g., toluene) solution of alcohol ROH is slowly added to an aromatic solvent (e.g., toluene) solution of $TiCl_4$, to avoid a large exotherm and to allow for the HCl gas produced to be vented carefully, and optionally neutralized. After the two reagents are combined and visible HCl evolution has ceased (or slowed), the reaction mixture may be heated to complete the reaction. For example, the reaction may be heated to about 100° C. or more for at least about 15 minutes to complete the reaction.

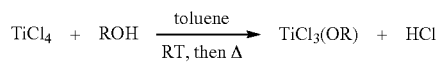

In an embodiment, the alcohol ROH is added to $TiCl_4$ and not in the reverse order, so as to keep $TiCl_4$ in excess during the addition.

The R group of the alcohol can be any suitable hydrocarbyl group, such as a primary, secondary or tertiary alkyl group or an aromatic group. The hydrocarbyl group R may itself be substituted further with one or more alkyl, aromatic or halide groups.

In an embodiment, the alcohol ROH is a primary or a secondary alcohol where R is a primary or secondary alkyl group having 1 to 20 carbon atoms.

In an embodiment, the alcohol ROH is a primary alcohol where R is a primary alkyl group having 1 to 10 carbon atoms. In an embodiment, the alcohol ROH is a primary alcohol where R is a methyl, ethyl, n-propyl, n-butyl, or n-pentyl. In an embodiment, the alcohol ROH is a primary alcohol where R is ethyl, n-propyl, or n-butyl. In an embodiment, the alcohol ROH is ethanol (R=ethyl). Methanol (R=Me) may also be used as the alcohol ROH in an embodiment.

In an embodiment, the alcohol ROH is a secondary alcohol where R is a secondary alkyl group having 3 to 21 carbon atoms. In an embodiment, the alcohol ROH is a secondary alcohol where R is iso-propyl, sec-butyl, or neo-pentyl. In an embodiment, the alcohol ROH is isopropanol (R=isopropyl).

A person skilled in the art will recognize that use of other suitable solvents, reaction temperatures and reaction times may also be used and optimized, and that such conditions are not limiting. Hence, the reaction time for Step 1, Option A is not specifically defined and will depend on various factors such as the reaction scale, temperature, solvent choice, reagent concentration and the like. In addition, the reaction temperature for Step 1, Option A is not specifically defined and will depend on various factors such as the reaction scale, time, solvent choice, reagent concentration and the like.

In an embodiment, Step 1, Option A is carried out above ambient (room) temperature. In an embodiment, Step 1, Option A is carried out above about 80° C. In an embodiment, Step 1, Option A is carried out above about 100° C.

In an embodiment, the $TiCl_3(OR)$ compound is formed in the presence of a suitable solvent such as but not limited to toluene or pentane, is not isolated and used directly in the next step (see Step 2 below).

In an embodiment, the $TiCl_3(OR)$ compound is formed in the presence of a suitable solvent such as but not limited to toluene or pentane, and is isolated by solvent removal.

In an embodiment, Step 1, Option A is carried out at a scale of at least about 400 mmol, or at least about 500 mmol, or at least about 1 mol.

Step 1: Preparation of $TiCl_3(OR)$, Option B.

$Ti(OR)_4$ is combined with $TiCl_4$ in the presence of a solvent, such as a hydrocarbon solvent, in an approximately 1:3 molar ratio, where R is defined as above. In an embodiment, an aromatic solvent (e.g., toluene) solution of $Ti(OR)_4$ is slowly added to an aromatic solvent (e.g., toluene) solution of $TiCl_4$.

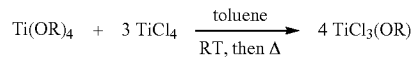

In an embodiment, $Ti(OR)_4$ is added to $TiCl_4$ and not in the reverse order, so as to keep $TiCl_4$ in excess during the addition.

A person skilled in the art will recognize that other suitable solvents, reaction temperatures and reaction times may also be used and optimized, and that such conditions are not limiting. Hence, the reaction time for Step 1, Option B is not specifically defined and will depend on various factors such as the reaction scale, temperature, solvent choice, reagent concentration and the like. In addition, the reaction temperature for Step 1, Option B is not specifically defined and will depend on various factors such as the reaction scale, time, solvent choice, reagent concentration and the like.

In an embodiment, Step 1, Option B is carried out above ambient (room) temperature. In an embodiment, Step 1, Option B is carried out above about 80° C. In an embodiment, Step 1, Option B is carried out above about 100° C.

In an embodiment, the $TiCl_3(OR)$ compound is formed in the presence of a suitable solvent such as but not limited to toluene or pentane, is not isolated and used directly in the next step (see Step 2 below).

In an embodiment, the TiCl$_3$(OR) compound is formed in the presence of a suitable solvent such as but not limited to toluene or pentane, and is isolated by solvent removal.

In some embodiments, Step 1, Option B is carried out at a scale of at least about 400 mmol, or at least about 500 mmol, or at least about 1 mol.

Step 2: Preparation of R$^1_3$P=N—TiCl$_3$.

TiCl$_3$(OR) is combined with an approximately equimolar amount of R$^1_3$P=N—SiMe$_3$ in the presence of a suitable solvent. The R$^1_3$P=N—SiMe$_3$ compound may be added directly, as a solid or as a solution in a suitable solvent such as but not limited to toluene. The TiCl$_3$(OR) may be present in a suitable solvent such as but not limited to toluene before combination with R$^1_3$—P=N—SiMe$_3$. The R$^1_3$P=N—SiMe$_3$ may be added slowly in batches. Following addition of R$^1_3$P=N—SiMe$_3$ the reaction mixture is heated to drive the reaction forward.

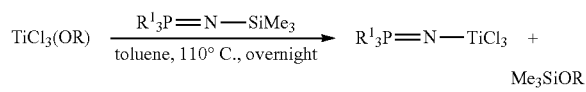

$$\text{TiCl}_3(\text{OR}) \xrightarrow[\text{toluene, 110° C., overnight}]{\text{R}^1_3\text{P}=\text{N}-\text{SiMe}_3} \text{R}^1_3\text{P}=\text{N}-\text{TiCl}_3 + \text{Me}_3\text{SiOR}$$

~1 mL of toluene/1 mmol of material

In an embodiment R$^1_3$P=N—SiMe$_3$ is added to TiCl$_3$(OR) and not in the reverse order, so as to keep TiCl$_3$(OR) in excess during the addition, although the opposite order of addition is also contemplated.

A person skilled in the art will recognize that other suitable solvents, reaction temperatures and reaction times may also be used and optimized, and that such conditions are not limiting. Hence, the reaction time for Step 2 is not specifically defined and will depend on various factors such as the reaction scale, temperature, solvent choice, reagent concentration and the like. In addition, the reaction temperature for Step 2 is not specifically defined and will depend on various factors such as the reaction scale, time, solvent choice, reagent concentration and the like.

In an embodiment, Step 2 is carried out above ambient (room) temperature. In an embodiment, the reaction mixture is stirred for at least about 12 hours at a temperature of at least about 80° C. In an embodiment, the reaction mixture is stirred for at least about 6 hours at a temperature of at least about 100° C. In an embodiment, the reaction mixture is stirred for at least about 6 hours at a temperature of at least about 110° C.

Depending on the reaction solvent used, the product R$^1_3$P=N—TiCl$_3$ may precipitate from the reaction solution and so may be isolated by filtration. For example, where R$^1$ is tert-butyl, the product precipitates from a solution of toluene.

Cooling the reaction mixture may cause product R$^1_3$P=N—TiCl$_3$ to precipitate from solution. If the product R$^1_3$P=N—TiCl$_3$ precipitates or crystallizes from solution, the product can be isolated by filtration and washed with suitable hydrocarbon solvents such as but not limited to toluene, pentane, heptane or mixtures thereof.

In an embodiment, R$^1$ is independently selected from a C$_{1-30}$ hydrocarbyl radical which is unsubstituted or further substituted by one or more halogen atoms, a C$_{1-20}$ alkyl radical, a C$_{1-8}$ alkoxy radical, a C$_{6-10}$ aryl radical, a C$_{6-10}$ aryloxy radical, an amido radical, a silyl radical, and a germanyl radical. In one embodiment, each R$^1$ is a C$_{1-20}$ alkyl radical, a C$_{1-8}$ alkoxy radical, a C$_{6-10}$ aryl radical, a C$_{6-10}$ aryloxy radical, an amido radical, a silyl radical, and a germanyl radical. In one embodiment each R$^1$ is a C$_{1-20}$ alkyl radical. In one embodiment, R$^1$ is selected from propyl, butyl, pentyl, hexyl and octyl. In one embodiment each R$^1$ group is a tertiary butyl group (t-butyl, t-Bu, tert-butyl, tert-Bu for short).

In an embodiment, where R$^1$ is tert-butyl, the t-Bu$_3$P=N—TiCl$_3$ product is prepared in greater than about 80% yield at over about 90% purity by $^1$H NMR over Steps 1 and 2.

In an embodiment, where R$^1$ is tert-butyl, the t-Bu$_3$P=N—TiCl$_3$ product is prepared in greater than about 90% yield at over about 95% purity by $^1$H NMR over Steps 1 and 2.

In embodiments, Step 2 is carried out at a scale of at least about 400 mmol, or at least about 500 mmol, or at least about 1 mol.

Step 3: Deprotonation of R$^2$-Indene, R$^2$—C$_9$H$_7$.

This step involves the removal of a proton from an indene molecule, for example, a 1-position substituted indene molecule. Although the deprotonation of indene molecules, whether substituted or unsubstituted is well known and can be carried out with a variety of suitable bases, we have found that the deprotonation of an indene molecule which bears a pentafluorophenyl benzyl moiety (C$_6$F$_5$CH$_2$—) can be difficult, unless carried out with a suitably non-nucleophilic and/or encumbered base.

Accordingly, in one embodiment a substituted indene molecule is deprotonated with a relatively non-nucleophilic sterically encumbered metal amide salt (relative to, for example, n-butyllithium). Such suitable amide salts may be selected from metal salts in which the anion is selected from the group comprising diisopropylamide, 2,2,6,6-tetramethylpiperidide, bis(trimethylsilyl)amide and the like. Metal cations can be any suitable cation such as lithium or sodium or potassium (Li$^+$, Na$^+$ or K$^+$).

Treatment of an indene molecule with a suitable base will provide an indenide metal salt. Such indenide anions are well known to be suitable ligands for transition metals and are most often referred to as indenyl ligands.

In an embodiment, the base used to deprotonate a substituted indene molecule is lithium diisopropyl amide (LDA) which has the formula [iso-Pr$_2$N][Li].

In an embodiment, the indene molecule will be singly substituted where the substituent is selected from a substituted or unsubstituted alkyl group, a substituted or an unsubstituted aryl group, and a substituted or unsubstituted benzyl (e.g., C$_6$H$_5$CH$_2$—) group. Suitable substituents for the alkyl, aryl or benzyl group may be selected from alkyl groups, aryl groups, alkoxy groups, aryloxy groups, alkylaryl groups (e.g., a benzyl group), arylalkyl groups and halide groups.

In an embodiment, the indene molecule will be a singly substituted indene, R$^2$-Indene, where the R$^2$ substituent is a substituted or unsubstituted alkyl group, a substituted or an unsubstituted aryl group, or a substituted or unsubstituted benzyl group. Suitable substituents for an R$^2$ alkyl, R$^2$ aryl or R$^2$ benzyl group may be selected from alkyl groups, aryl groups, alkoxy groups, aryloxy groups, alkylaryl groups (e.g., a benzyl group), arylalkyl groups and halide groups.

In an embodiment, the indene molecule will have at least a 1-position substituent (1-R$^2$) where the substituent R$^2$ is a substituted or unsubstituted alkyl group, a substituted or an unsubstituted aryl group, or a substituted or unsubstituted benzyl group. Suitable substituents for an R$^2$ alkyl, R$^2$ aryl or R$^2$ benzyl group may be selected from alkyl groups, aryl groups, alkoxy groups, aryloxy groups, alkylaryl groups (e.g., a benzyl group), arylalkyl groups and halide groups.

In an embodiment, the base used to deprotonate a 1-position substituted indene molecule (1-R$^2$-indene or 1-R$^2$—C$_9$H$_7$) is lithium diisopropyl amide (LDA) which has the formula [iso-Pr$_2$N][Li].

In an embodiment, the deprotonation reaction takes place in the presence of a suitable aromatic solvent such as toluene at ambient (room) temperature.

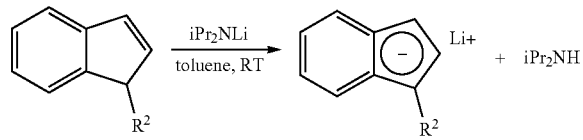

A person skilled in the art will recognize that other suitable solvents, various reaction temperatures and various reaction times may be used and optimized, and that such conditions are not limiting. Hence, the reaction time for Step 3 is not specifically defined and will depend on various factors such as the reaction scale, temperature, solvent choice, reagent concentration and the like. In addition, the reaction temperature for Step 3 is not specifically defined and will depend on various factors such as the reaction scale, time, solvent choice, reagent concentration and the like.

In an embodiment, the deprotonation reaction is carried out at ambient (room) temperature (as opposed to low temperatures such as those below room temperature or below about 0° C., or at or below about −30° C., or at or below about −40° C.).

In an embodiment, the indene molecule will be a singly substituted, 1-$R^2$-Indene where the substituent $R^2$ is in the 1-position of the indene molecule and $R^2$ is a substituted or unsubstituted alkyl group, a substituted or unsubstituted aryl group, or a substituted or an unsubstituted benzyl group. Suitable substituents for an $R^2$ alkyl, $R^2$ aryl or $R^2$ benzyl group may be selected from alkyl groups, aryl groups, alkoxy groups, aryloxy groups, alkylaryl groups (e.g., a benzyl group), arylalkyl groups and halide groups.

In an embodiment, the indene molecule will be singly substituted at the 1 position, 1-$R^2$-Indene, where the substituent $R^2$ is a (partially/fully) halide substituted alkyl group, a (partially/fully) halide substituted benzyl group, or a (partially/fully) halide substituted aryl group.

In an embodiment, the indene molecule will be singly substituted at the 1 position, 1-$R^2$-Indene, where the substituent $R^2$ is a (partially/fully) halide substituted benzyl group.

When present on an indene molecule, a benzyl group can be partially or fully substituted by halide atoms, for example, fluoride atoms. The aryl group of the benzyl group may be a perfluorinated aryl group, a 2,6 (i.e., ortho) fluoro substituted phenyl group, 2,4,6 (i.e., ortho/para) fluoro substituted phenyl group or a 2,3,5,6 (i.e., ortho/meta) fluoro substituted phenyl group respectively. The benzyl group is, in an embodiment, located at the 1 position of the indene molecule.

In an embodiment, the indene molecule will be a singly substituted indene, 1-$R^2$-indene, where the substituent $R^2$ is a pentafluorobenzyl ($C_6F_5CH_2$—) group.

In an embodiment, 1-$C_6F_5CH_2$-indene (1-$C_6F_5CH_2$—$C_9H_7$) is deprotonated with LDA to give [Li][1-$C_6F_5CH_2$-indenide]([Li][1-$C_6F_5CH_2$—$C_9H_6$]).

In an embodiment, 1-$C_6F_5CH_2$-indene (1-$C_6F_5CH_2$—$C_9H_7$) is deprotonated with LDA at ambient (room) temperature in the presence of a suitable solvent such as but not limited to toluene to give [Li][1-$C_6F_5CH_2$-indenide] ([Li][1-$C_6F_5CH_2$—$C_9H_6$]).

In an embodiment, 1-$C_6F_5CH_2$-indene (1-$C_6F_5CH_2$—$C_9H_7$) is deprotonated with LDA at ambient (room) temperature in the presence of a suitable solvent such as but not limited to toluene to give [Li][1-$C_6F_5CH_2$-indenide] ([Li][1-$C_6F_5CH_2$—$C_9H_6$]) and the [Li][1-$C_6F_5CH_2$-indenide] solution is used directly in the next step (see Step 4 below).

In an embodiment, Step 3 is carried out at a scale of at least about 400 mmol, or at least about 500 mmol, or at least about 1 mol.

In an embodiment, the $R^2$-indenide metal salt is formed in the presence of a suitable solvent such as but not limited to toluene, or an ethereal solvent, is not isolated, and used directly in the next step (see Step 4 below).

In an embodiment, the 1-$R^2$-indenide metal salt is formed in the presence of a suitable solvent such as but not limited to toluene, or an ethereal solvent, is not isolated, and used directly in the next step (see Step 4 below).

In an embodiment, the [Li][1-$C_6F_5CH_2$-indenide] salt is formed in the presence of a suitable solvent such as but not limited to toluene, is not isolated, and used directly in the next step (see Step 4 below).

Step 4: Metallation of a $R^2$-Indenide Ligand.

An indenide salt [Li][$R^2$-indenide] where $R^2$ is defined as above may be employed as a ligand precursor, which on reaction with $R^1_3P$=N—$TiCl_3$ where $R^1$ is defined as above, becomes ligated to a metal center (i.e., a bond is formed between at least one atom, for example, a carbon atom, of the ligand and the metal). In one embodiment, the indenyl ligand will bond to the metal via a five carbon ring which is bonded to the metal via eta-5 (or in some cases eta-3) bonding.

In an embodiment, [Li][$R^2$-indenide] is reacted with a phosphinimide ligated titanium metal chloride $R^1_3P$=N—$TiCl_3$ (prepared as above) to give a phosphinimide coordination compound ($R^2$-Indenyl)Ti(N=$PR^1_3$)$Cl_2$.

In an embodiment, [Li][1-$R^2$ indenide] is reacted with a phosphinimide ligated titanium metal chloride $R^1_3P$=N—$TiCl_3$ (prepared as above) to give a phosphinimide coordination compound (1-$R^2$-Indenyl)Ti(N=$PR^1_3$)$Cl_2$.

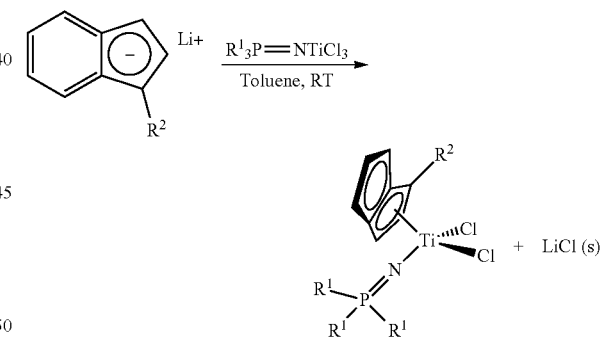

In an embodiment, [Li][1-$R^2$ indenide] is added to a phosphinimide ligated titanium metal chloride $R^1_3P$=N—$TiCl_3$ (prepared as above), and not in the reverse order, to give a phosphinimide coordination compound (1-$R^2$-Indenyl)Ti(N=$PR^1_3$)$Cl_2$.

Coordination compounds of the type (1-$R^2$-indenyl)($R^1_3P$=N)$TiCl_2$ are known to be suitable catalyst components for polymerizing ethylene, optionally with alpha-olefins, to make ethylene polymers or copolymers.

In an embodiment, the metallation reaction is carried out in toluene.

In an embodiment, the metallation reaction is carried out in hydrocarbon solvent such as heptane.

In an embodiment, the metallation reaction is carried out at ambient (room) temperature, in a hydrocarbon solvent.

In an embodiment, the metallation reaction is carried out at elevated temperature, for example at about 40° C. to about 90° C. in a hydrocarbon solvent.

A person skilled in the art will recognize other suitable solvents, reactions temperatures and reaction times may also be used and optimized, and that such conditions are not limiting. Hence, the reaction time for Step 4 is not specifically defined and will depend on various factors such as the reaction scale, temperature, solvent choice, reagent concentration and the like. In addition, the reaction temperature for Step 4 is not specifically defined and will depend on various factors such as the reaction scale, time, solvent choice, reagent concentration and the like.

In an embodiment, Step 4 is carried out at a scale of at least about 400 mmol, or at least about 500 mmol, or at least about 1 mol.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 70% yield at over about 80% purity by $^1H$ NMR over Steps 3 and 4.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 75% yield at over about 85% purity by $^1H$ NMR over Steps 3 and 4.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 80% yield at over about 90% purity by $^1H$ NMR over Steps 3 and 4.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 85% yield at over about 90% purity by $^1H$ NMR over Steps 3 and 4.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 90% yield at over about 95% purity by $^1H$ NMR over Steps 3 and 4.

In an embodiment, where $R^1$ is tert-butyl, and $R^2$ is $C_6F_5CH_2$— the $(1-R^2\text{-Indenyl})Ti(N=PR^1_3)Cl_2$ product is prepared in greater than an about 90% yield at over about 99% purity by $^1H$ NMR over Steps 3 and 4.

In an embodiment, $R^1$ is tert-butyl, and $R^2$ is $C_6F_5CH_2$, and Steps 1-4 are all carried out in a single solvent such as but not limited to toluene.

In an embodiment, $R^1$ is tert-butyl, and $R^2$ is $C_6F_5CH_2$, and Steps 1-4 are all independently carried out at temperatures which are at or above ambient (room) temperature.

In an embodiment, $R^1$ is tert-butyl, and $R^2$ is $C_6F_5CH_2$, and Steps 1-4 are all carried out in toluene at temperatures which are at ambient (room) temperature or above.

Some embodiments of the invention will further be described by reference to the following examples. The following examples are merely illustrative and are not intended to be limiting. Unless otherwise indicated, all percentages are by weight unless otherwise specified.

EXAMPLES

General Conditions

All reactions involving air and or moisture sensitive compounds were conducted under nitrogen using standard Schlenk techniques, or in a glovebox. Toluene, heptane and pentane were purified using the system described by Pangborn, Grubbs, et. al. in Pangborn, A. B; Giardello, M. A.; Grubbs, R. H; Rosen, R. K.; Timmers, F. J. *Organometallics* 1996, 15, 1518. Tetrahydrofuran was purified by passing it through a column of activated alumina, and pentane and the other solvents were stored over activated 4 Å sieves. All chemicals were purchased from Aldrich and used without further purification. Deuterated solvents were purchased from CIL (THF-$d_8$, toluene-$d_8$) and were stored over 4 Å sieves. NMR spectra were recorded on Bruker spectrometer (400.1 MHz for $^1H$, 162 MHz for $^{31}P$, 376 MHz for $^{19}F$).

Preparation of Lithium Diisopropylamide (LDA). n-BuLi (1.6 M, 32 mmols, 20 mL) was added to a pentane solution (~150 mL) of diisopropylamine $iPr_2NH$ (dried over mol sieves and distilled, 20 mmols, 3.24 g) at room temperature. No apparent heat generation was observed. The mixture was stirred for 1 hour to produce a clear solution. Pentane was pumped away under vacuum. The product solidified during pentane removal and at that point, evacuation was terminated allowing the product to further crystallize for 3 hours. The solid product lithium diisopropylamide, $LiN(iPr_2)$ (LDA) was isolated by filtration, washed with pentane and dried under vacuum. The solid weighed 2.8 g.

Preparation of t-$Bu_3P$=$NSiMe_3$. This compound was prepared by reaction of tri tert-butylphosphine (t-$Bu_3P$) with trimethylsilylazide ($Me_3SiN_2$). Preparation of t-$Bu_3P$=N—$SiMe_3$ was reported in the following: Courtenay, S.; Ong, C. M.; Stephan, D. W. *Organometallics*, 2003, 22, 818-825.

Ti(OEt)$_4$ (where Et is short for ethyl) was purchased from commercial sources.

Part A: Preparation of t-$Bu_3P$=N—$TiCl_3$

Comparative Example 1

Preparation of t-$Bu_3P$=N—$TiCl_3$ from $TiCl_4$ at Small Scale (<5 mmol). $TiCl_4$ (0.5 g, 2.63 mmols) was added to a toluene solution (40 mL) of t$Bu_3P$=N—$SiMe_3$ (760 mg, 2.63 mmol) in a 100 mL Schlenk flask. The orange solution was stirred at ambient (room) temperature for 7 hours. No obvious reaction was observed as the color of the solution was still orange. The solution was refluxed at 110° C. overnight. The orange solution became almost colorless. The solvent was pumped off to give pure t-$Bu_3P$=N—$TiCl_3$ as crystalline solid in 100% yield (0.97 g. $^1H$ NMR, $\delta$(toluene-$d_8$): 1.08 (d, J=14 Hz); $^{31}P$ NMR, $\delta$(toluene-$d_8$): 55.2 (s), chemical shift calibrated.

Comparative Example 2

Preparation of t-$Bu_3P$=N—$TiCl_3$ from $TiCl_4$ at Larger Scale (>25 mmol). A toluene solution (30 mL) of t$Bu_3P$=N—$SiMe_3$ (7.63 g, 26.3 mmol) was added to $TiCl_4$ (5.0 g, 26.3 mmols) in toluene (20 mL). A dark red solution formed. The total reaction volume was about 70 mL after rinsings were added to the 100 mL reaction flask. After being stirred at room temperature for 0.5 hours, the solution was heated to 110° C. After 16 hours, the solution was still dark orange. The color of the solution was checked at 24 hours and 36 hours. The dark orange color did not disappear. The solution was pumped to remove toluene. The residue was washed with cold toluene (about 0° C., 2×20 mL) and then pentane (2×20 mL). 1.8 g of pure product was isolated. The yield was only 18.4%.

By examining the yields of t-$Bu_3P$=$NTiCl_3$ obtained in Comp. Examples 1 and 2, it is apparent that the yield is heavily diminished as the scale of the reaction is increased. Without wishing to be bound by theory, it is believed that the above reaction is catalyzed by adventitious water, and that as the reaction scale increases, the relative amount of water available to catalyze the reaction decreases, leading to a lower yield.

Comparative Example 3a

Preparation of t-Bu$_3$P=N—TiCl$_3$ in the presence of deliberately added water. Comp. Example 2 was repeated with the exception that 110 mg of Al$_2$(SO$_4$)$_3$.18H$_2$O was added to the reaction after the two reactants were mixed. The solution was then heated to 115° C. and the reaction was stirred overnight. A brown solution with an insoluble solid was generated. The reaction was filtered while still hot. The filtration was very difficult as some of the product t-Bu$_3$P=N—TiCl$_3$ (which has poor solubility in toluene) crystallized in the pores of the filter frit. The insoluble solid was rinsed with hot toluene (~20 mL), then pentane (2×10 mL) and was discarded (1.98 g). The filtrate and the hot washings were pumped to about 15 mL (while a lot of solid crystallized) and were chilled in a freezer overnight. The mother liquor was decanted. The solid was washed with pentane and dried under vacuum. The yield was 6.9 g of beige solid (71%) and the product was pure by NMR.

Comparative Example 3b

Comparative example 3a was repeated under the same reaction conditions and same reaction scale. With very difficult hot filtration, the reaction produced 3.1 g of greenish insoluble by-product and 5.4 g of impure product.

Comparative Example 4

Preparation of t-Bu$_3$P=N—TiCl$_3$ in the presence of added t-Bu$_3$P=NH and water at larger scale (ca. 200 mmol). TiCl$_4$ (39.62 g, 208.8 mmols, in 200 mL of toluene) was added to a dried toluene solution of t-Bu$_3$P=NSiMe$_3$ (100 g solution, 55 weight % (wt %), 55 g, 190 mmols). The color of the mixture became brown. Toluene was added so that the total volume of the solution was made to about 400 mL. t-Bu$_3$P=NH (4.1 g, 18.86 mmols, which was thought to accelerate the reaction) was added to take the total amount of ligand to 208.86 mmols. The reaction was stirred while the heating bath temperature was raised to 115° C. Lots of solid precipitated. Within 1.5 hours, the reaction turned to dark red with only a very small amount of solid present. The reaction was heated overnight to produce a slurry (insoluble solid was present). The color of the reaction was still red indicating that the reaction was incomplete. Al$_2$(SO$_4$)$_3$.18H$_2$O (354 mg) was slowly added over a 3 hour period. The color of the reaction changed from red to brown. The hot reaction mixture was filtered in order to remove the insoluble brown solid. The filtration was very difficult as the product crystallized very easily from the hot solution and it began to plug the glass filter frit. Hot toluene had to be used several times to rinse the glass frit and to keep the filtration going. The insoluble brown solid over the frit was discarded. The light brown filtrate (with crystallized product) was cooled to ambient (room) temperature and chilled at −20° C. for 5 hours. The solid was isolated by filtration and was washed with toluene/heptane (50/50, 100 mL) and was dried under vacuum. The yield was 34.24 g (44%) and the product was pure by NMR.

By examining the yield and purity of the product t-Bu$_3$P=N—TiCl$_3$ as well as the filtration difficulty for the procedures given in Comp. Examples 3 and 4 it is apparent that the yield and purity can be poor for larger scale reactions and that the filtration to remove impurities is difficult and time consuming.

Inventive Example 1

Preparation of t-Bu$_3$P=N—TiCl$_3$ from TiCl$_3$(OEt), Procedure 1 (ca. 180 mmol). Preparation of TiCl$_3$(OEt). EtOH (dried with NaOEt and distilled, 8.25 g, 179.07 mmol) in toluene (~50 mL in a vial) was added to a toluene solution (100 mL) of TiCl$_4$ (33.97 g, 179.07 mmol) slowly at room temperature. The slow rate of addition was carefully controlled to avoid a large exotherm and to slowly vent the HCl gas formed to a bubbler. After the addition, the vial containing the EtOH was rinsed with toluene (2×10 mL) and the rising were added to the reaction flask. The reaction mixture was then heated to 100° C. for 45 mins to drive off any remaining HCl and to complete the reaction. The color of the solution changed from red to light orange. Preparation of t-Bu$_3$P=N—TiCl$_3$. In a glove box, solid t-Bu$_3$P=N—SiMe$_3$ (51.84 g, 179.07 mmol) was added in batches, each over a 20 minute period, to the TiCl$_3$(OEt) solution obtained above and which had been allowed to cool to room temperature. The solution became dark red. The reaction was stirred and heated at 110° C. overnight. Crystalline product precipitated during the reaction. The content of the reaction was cooled to RT and chilled at −20° C. for 3 hours. The solid was isolated by filtration and was washed with a 50/50 toluene/heptane mixture (2×30 mL), then pentane (30 mL), and dried under vacuum. $^1$H and $^{31}$P NMR indicated that the product was pure. The yield was 57 g (86%). $^1$H NMR, δ(toluene-d$_8$): 1.11 (d, J=14 Hz); $^{31}$P NMR, δ(toluene-d$_8$): 55.3 (s), chemical shift calibrated. It is recommended that for procedure 1, the formation of TiCl$_3$(OEt) is driven to completion by heat and enough reaction time before the addition of t-Bu$_3$P=NSiMe$_3$.

A person skilled in the art will immediately recognize by comparing Inv. Example 1, with Comp. Examples 1-4, that use of TiCl$_3$(OEt) in place of TiCl$_4$ provides the desired product t-Bu$_3$P=N—TiCl$_3$ in higher yield and higher purity even at an ca. 180 mmol scale.

Verification:

The above reactions were repeated by a second experimenter at a scale of 46 mmol. The solution which was formed by adding EtOH to TiCl$_4$ was heated at 100° C. for 30 minutes and cooled to room temperature. The t-Bu$_3$P=N—SiMe$_3$ was added as a toluene solution to the TiCl$_3$(OEt) in toluene. The yield was 87% and the product was pure by $^1$H and $^{31}$P NMR.

Alternative Solvent for TiCl$_3$(OEt) Formation:

To form TiCl$_3$(OEt) in pentane EtOH was added to a presealed vial. The weight of EtOH added was 2.294 g (49.8 mmol). Pentane (~20 mL) was then added to the vial to make an EtOH solution. This solution was added slowly to a pentane solution (~50 mL) of TiCl$_4$ (9.45 g, 49.8 mmol) in a 250 mL Schlenk flask. After the addition, pentane was pumped off to give solid TiCl$_3$(OEt). Solid t-Bu$_3$P=N—SiMe$_3$ (14.3 g, 49.5 mmol) was added to the flask and toluene (~60 mL) was added. This solution was red in color, and was refluxed overnight. The solution was chilled in the freezer (−20° C.) for 2 hours, and a precipitated solid was isolated by filtration and washed with toluene/heptane (50/50) (2×60 mL), then with pentane and dried. The yield was 15.9 g, 87% and the product was pure by $^1$H and $^{31}$P NMR.

Inventive Example 2

Preparation of t-Bu$_3$P=N—TiCl$_3$ from TiCl$_3$(OEt). Procedure 2. Preparation of TiCl$_3$(OEt). In a fume hood, Ti(OEt)$_4$ (5.703 g 25 mmols) was added to a toluene (60 mL) solution of TiCl$_4$ (14.228 g, 75 mmol). The bright orange solution turned light orange. The mixture was heated at 100° C. for 1.5 hours and cooled to room temperature. The flask was brought into a glove box for the next step. Preparation of t-Bu$_3$P=N—TiCl$_3$. t-Bu$_3$P=N—SiMe$_3$ (28.95 g, 100 mmol) in toluene (~100 mL) was added to the solution of TiCl$_3$(OEt) obtained in the preceding step. The color of the solution turned to red brown. The reaction was heated at 110° C. overnight. Crystalline solid was observed in the hot light greenish solution, which was then cooled to room temperature. More solid crystalized. The flask was chilled at –20° C. for 2 hours and the solid was isolated by filtration, washed with a mixture of toluene/heptane (50/50), pentane and dried under vacuum. The yield was 37 g (99% yield) and the product was pure by $^1$H and $^{31}$P NMR. The procedure works best by adding Ti(OEt)$_4$ to neat TiCl$_4$ or to TiCl$_4$ as a solution in toluene, followed by heating the mixture at 100° C. or more for a few hours. This gives TiCl$_3$(OEt) as a single product. On the other hand, if TiCl$_4$ is added to Ti(OEt)$_4$ or if the reaction mixture is not heated to more than 80° C. substantial amounts of TiCl$_2$(OEt)$_2$ or TiClx(OEt)y (where x is not 3 and y is not 1) may form in addition to the desired TiCl$_3$(OEt) product. Indeed, it is recommended that for procedure 2, the formation of TiCl$_3$(OEt) is driven to completion by heat and enough reaction time before the addition of tBu$_3$P=NSiMe$_3$.

A person skilled in the art will immediately recognize by comparing Inv. Example 2, with Comp. Examples 1-4, that use of TiCl$_3$(OEt) in place of TiCl$_4$ provides the desired product t-Bu$_3$P=N—TiCl$_3$ in higher yield and higher purity and without difficult filtration steps.

Inventive Example 3

Large Scale Preparation (500 mmol) of t-Bu$_3$P=N—TiCl$_3$ from TiCl$_3$(OEt). In a one liter, two necked round bottomed flask was weighed 209.65 g of TiCl$_4$ (1.124 moles. 3.4% excess) and 450 mL of toluene. One of the necks was fitted with a septum and the other one with a condenser. At the top of the condenser, a three-way nitrogen lines run from a nitrogen-vacuum manifold to the condenser and to an oil bubbler and a Na$_2$CO$_3$/water solution bubbler. Absolute ethanol (dried with Na and distilled, 50.096 g, 1.087 moles) in 25 mL of toluene was added slowly to the flask at 0° C. Fuming was observed. The addition took 20 minutes. Although the reaction between TiCl$_4$ and EtOH produced some HCl and caused fuming, the reaction was slow at 0° C. The reaction was heated to 50° C. and maintained at this temperature for about 0.5 hour. Vigorous generation of HCl gas was observed. The reaction temperature was slowly increased to 100° C. and was maintained at 100° C. overnight. A small sample of the orange solution was pumped to dryness under vacuum to give a white solid. $^1$H NMR showed that there was only one ethyl environment, and so the reaction was complete and produced only TiCl$_3$(OEt)). No further generation of HCl gas was observed at this time. Although the solution could be used directly for reaction with t-Bu$_3$P=N—SiMe$_3$ in order to form t-Bu$_3$P=N—TiCl$_3$, the TiCl$_3$(OEt) material was isolated by removing solvent under vacuum to give pure TiCl$_3$(OEt). $^1$H NMR, δ(toluene-d$_8$), 3.82 ppm, q, J=6.7 Hz, 0.83 ppm, t, J=6.7 Hz. TiCl$_3$(OEt) (99.65 g, 500 mmols) was weighed into a 1 liter flask and 500 mL of toluene was added. Next, t-Bu$_3$P=N—SiMe$_3$ (144.75 g, 500 mmols) was added as solid. Fuming was observed indicating the Bu$_3$P=N—SiMe$_3$ contained some moisture. The fumes were purged by nitrogen several times during the addition. The red solution formed was stirred for 1.5 hours at room temperature and was heated to 110° C. for 21 hours. The reaction was allowed to cool to ambient (room) temperature and was filtered. The solid present at this time was collected by filtration and was washed with toluene (2×50 mL) and pentane (50 mL). The solid (183.2 g vs 185 g of theoretical yield) was almost colorless with a few slightly yellow crystals. $^1$H and $^{31}$P NMR indicated that the product was almost pure (~95%). This purity level is sufficient to employ the product in a metallation reaction to form (C$_6$F$_5$CH$_2$Ind)(t-Bu$_3$P=N)TiCl$_2$ (see Inv. Example 7 below). However, if desirable, the purity of the product could be improved by stirring with TiCl$_4$ (23.9 g) in 500 mL of toluene at 100° C. over a weekend. The slurry was cooled to room temperature and was filtered. The solid over the frit was washed with toluene (2×60 mL), pentane (2×60 mL) and was dried by vacuum (158 g, 85% yield). $^1$H and $^{31}$P NMR showed that the product t-Bu$_3$P=N—TiCl$_3$ was pure.

In view of Inv. Example 3, a person skilled in the art will immediately recognize that use of TiCl$_3$(OEt) in place of TiCl$_4$ provides the desired product t-Bu$_3$P=N—TiCl$_3$ in high yield and high purity at a commercially relevant scale of 500 mmol.

Reaction Scheme

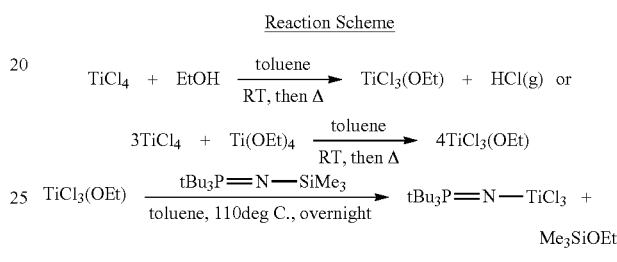

~1 mL of toluene/1 mmol of material

Part B: Preparation of (1-C$_6$F$_5$CH$_2$Ind)(t-Bu$_3$P=N)TiCl$_2$

Comparative Examples 5a-5e for the Preparation of 1-C$_6$F$_5$CH$_2$IndLi

Comp. 5a. n-BuLi (normal-butyl lithium, 1.6 M in hexanes, 4.54 mL, 7.26 mmols) was added dropwise to a solution of 1-C$_6$F$_5$CH$_2$Indene in heptane (40 mL) at room temperature. The solution was stirred for 48 hours. Except for a very small amount of sticky material formed on the wall of the reaction flask, the material in the bulk solution was shown by $^{19}$F NMR to be the unreacted starting material 1-C$_6$F$_5$CH$_2$Indene (1-C$_6$F$_5$CH$_2$C$_9$H$_7$). Comp. 5b. n-BuLi (1.6 M in hexanes, 3.2 mL, 5 mmols) was added dropwise over ten minutes in a toluene solution (~60 mL) of 1-C$_6$F$_5$CH$_2$Indene at 0° C. The solution was stirred for 2 hours at 0° C. $^{19}$F NMR showed significant amount of unreacted starting material 1-C$_6$F$_5$CH$_2$Indene and an un-identified by-product species. Comp. 5c. The reaction between n-BuLi and 1-C$_6$F$_5$CH$_2$Indene was conducted at 0° C. in 1,2-dimethoxyethane for 2 hours and stirred overnight at room temperature. $^1$H NMR showed a number of species present in the reaction mixture. Comp. 5d. n-BuLi (1.6 M in hexanes, 3.2 mL, 4 mmols) was added dropwise at room temperature in 8 minutes to a solution of 1-C$_6$F$_5$CH$_2$Indene (1.184 g, 4 mmols) and 1,2-dimethoxyethane (0.361 g, 4 mmols) in heptane (~40 mL). The color of the solution turned gold. White precipitate formed from the clear solution. After being stirred overnight at room temperature the slurry turned slight yellow in color. The solid was isolated by filtration, washed with pentane and dried under vacuum. $^{19}$F NMR showed that the product 1-C$_6$F$_5$CH$_2$IndenylLi (i.e. [Li][1-C$_6$F$_5$CH$_2$indenide] or [Li][1-C$_6$F$_5$CH$_2$C$_9$H$_6$]) formed with about 90% purity (10% was decomposed). The reaction was repeated a few times. However, the result was not reproducible in each attempt. Comp. 5e. n-BuLi in hexanes was added to equal-molar amount of 1-$C_6F_5CH_2$Indene at –40° C. in THF. 1-$C_6F_5CH_2$IndenylLi formed quantitatively. The solution was warmed to 7° C. and was quenched with $Me_3SiCl$. The desired product 1-$C_6F_5CH_2$-3-$Me_3Si$-indene formed. However, when n-BuLi in hexanes was added to 1-$C_6F_5CH_2$Indene at –10° C. in THF, severe decomposition was observed.

Comp. Examples 5a and 5b, show that efforts to make the 1-$C_6F_5CH_2$Indenide anion by deprotonation with n-BuLi in the presence of non-polar hydrocarbon solvents such as pentane, heptane and toluene led to no or partial reaction, or to unknown side products. Examples 5c and 5d, led to reactions which produced impurities and which were difficult to reproduce. Example 5e which was conducted at low temperature (–40° C.) in THF was successful, but when higher temperatures were used (–10° C.), severe decomposition occurred.

Comparative Example 6

Preparation of (1-$C_6F_5CH_2$Ind)(t-$Bu_3P$=N)$TiCl_2$ from In Situ Generation of 1-$C_6F_5CH_2$IndLi in THF with n-BuLi 1-Pentafluorobenzyl indene (1-$C_6F_5CH_2$indene) (44.45 g, 150.2 mmol) was dissolved in THF (500 mL) and cooled to –40° C. 1.6 M n-Butyllithium in hexanes (93.75 mL, 150.0 mmol) was added dropwise to the flask over the course of 2 hours to yield a dark red reaction mixture. The reaction was stirred at –40° C. for one hour, and a cold (–40° C.) slurry of t-$Bu_3PNTiCl_3$ (55.59 g, 150.0 mmol) in THF (500 mL) was added dropwise over 2 hours. After the addition, the reaction mixture was allowed to warm to room temperature overnight. In the morning, the volatiles of the orange slurry were removed in vacuo, and the reaction solids were transferred to the glovebox, triturated with pentane, and dried in vacuo. The reaction solids were then dissolved in hot (70° C.) toluene and filtered through celite to remove the LiCl salt. The celite was thoroughly extracted with hot toluene until the filtrate colour changed from orange to colourless. The volume of the filtrate was reduced in vacuo, yielding a sticky orange product. This product was triturated with pentane and collected by filtration to yield fine orange crystals. The crude product was dried in vacuo below 200 mTorr (approximately 60 g, 95.2 mmol, 63.5%). NMR spectroscopy indicated approximately 10% of impurities consisting of unreacted t-$Bu_3PNTiCl_2$ as well as the undesirable product (1-$C_6F_5CH_2$Ind)(t-$Bu_3P$=N)$_2$TiCl. These products could be extracted away from the desired product (1-$C_6F_5CH_2$Ind)(t-$Bu_3P$=N)$TiCl_2$. The final product was over 95% pure by $^1$H NMR (54.00 g, 85.7 mmol, 57.1%).

A person skilled in the art will realize from Comp. Example 6 (as well as Comp. Examples 5a-5e), that due to the poor stability of the pentafluorobenzyl indenide salt obtained with n-BuLi in THF solution, that the deprotonation, and subsequent metallation reaction sequence must be carried out at low temperature (i.e., at least –40° C.) and in a coordinating solvent such as THF to give the desired end product in reasonable yield. The use of low temperature is less desirable for reactions carried out at a commercial scale.

Inventive Example 4

Preparation of 1-$C_6F_5CH_2$IndLi with LDA; NMR Scale

1-$C_6F_5CH_2$Indene (59 mg, 0.2 mmol) and LDA (21 mg, 0.2 mmol) were weighed in a 10 mL vial in a glove box. Toluene-$d_8$ (~3 mL) was added. The content was shaken to mix the slurry well. $^{19}$F NMR was taken at 45 mins. Approximately 99% conversion was observed at this time. $^{19}$F NMR was taken at 2.5 hours and 100% conversion was observed. The solution was kept at room temperature for 3 days and no change of the $^{19}$F NMR spectrum was observed. This demonstrated both the validity of using LDA as a base for the deprotonation of 1-$C_6F_5CH_2$Indene and the thermal stability of the product lithium indenide salt in toluene. $^{19}$F NMR, δ(toluene-$d_8$): –146.4 (m, 2F), –161.7 (t, 1F), –165.2 (m, 2F).

Inventive Example 5

Preparation of 1-$C_6F_5CH_2$IndLi with LDA; 10 mmol Scale $iPr_2NLi$ (1.186 g, 11 mmol) was weighed into a 200 mL Schlenk flask. Toluene (~50 mL) was added to the flask to make a slurry. 1-$C_6F_5CH_2$Indene (3.280 g, 11 mmol) was dissolved in about 40 mL of toluene and added into the flask. The reaction was stirred at room temperature for 3 hours. $^{19}$F NMR in toluene-$d_8$ showed that the conversion was 100%. The lithium salt need not be isolated and can be used directly in a metallation reaction.

In view of Inv. Examples 4 and 5, a person skilled in the art will recognize that the 1-$C_6F_5CH_2$IndLi indenide salt is readily formed using LDA as a base and provides a stable product. This is an improvement over deprotonation attempts with nBuLi as shown by Comparative Examples 5a-5e. Without wishing to be bound by theory, it appears that use of relatively unencumbered, nucleophilic base such as n-BuLi, leads to decomposition of the starting material and perhaps the reaction product as it forms, likely through nucleophilic attack of the n-Bu based carbanion to displace the fluorine group(s) present on the aromatic ring of the 1-$C_6F_5CH_2$-indene molecule. Also, use of LDA leads to the relatively coordinating molecule diisopropylamine $HNiPr_2$ which may help to stabilize the desired indenide 1-$C_6F_5CH_2$IndLi species and to help solubilize the same in the reaction solvent. As a result, the synthesis of the 1-$C_6F_5CH_2$IndLi salt could be scaled up as shown in Inventive Example 7.

Inventive Example 6

Preparation of (1-$C_6F_5CH_2$Ind)(t-$Bu_3P$=N)$TiCl_2$

The 1-$C_6F_5CH_2$IndLi solution made in Inv. Example 5 was added to a solution of t-$Bu_3PNTiCl_3$ (4.103 g, 11 mmol) in toluene (50 mL) over 20 minutes. The reaction mixture was stirred at room temperature overnight. A small portion of the reaction mixture was removed and pumped to dryness. About 2 mL of toluene-$d_8$ was added to the residue to dissolve the solid. The solution was filtered and the filtrate was used for $^1$H, $^{31}$P and $^{19}$F NMR analysis which showed that product was >98% pure. Workup of the bulk reaction mixture: The solid present was allowed to settle to the bottom of the flask and the supernatant was passed through a glass filter frit. The remaining solid was dissolved in $CH_2Cl_2$ (~30 mL) and also passed through a glass filter frit to remove LiCl salt. The combined filtrates (toluene and $CH_2Cl_2$) were pumped under vacuum to remove the $CH_2Cl_2$ and most of the toluene. During this process, the product began to crystallize. Solvent removal was halted and the resulting slurry was left overnight at room temperature. The product slurry was filtered through a glass filter frit and the solid was retained and washed with a mixture of toluene and heptane (60/40) (2×20 mL) and then pentane (20 mL). The product (1-$C_6F_5CH_2$Ind)(t-$Bu_3P$=N)

TiCl$_2$ was a bright orange-yellow crystalline solid. The yield was 6.09 g (94%). $^1$H, $^{19}$F and $^{31}$P NMR analysis showed that the product was pure. $^{19}$F NMR, δ(toluene-d$_8$): 145.2 (dd, 2F), 159.5 (dd, 1F), 164.5 (m, 2F). $^{31}$P NMR, δ(toluene-d$_8$): 45.8 (s). $^1$H NMR, δ(toluene-d$_8$): 7.96 (m, 1H), 7.60 (m, 1H), 7.16 (m, 2H), 6.88 (m, 1H), 6.50 (m, 1H), 4.57 (d, J=14 Hz, 1H), 4.08 (d, J=14 Hz), 2.14 (s, 3H), 1.20 (d, J=14 Hz, 27H).

Inventive Example 7

Preparation of (1-C$_6$F$_5$CH$_2$Ind)(t-Bu$_3$P=N)TiCl$_2$ at a Large Scale (ca. 400 mmol)

In-situ LDA Synthesis: iPr$_2$NH (42.776 g, 423 mmol) was weighed in a 2 L round bottomed flask and 300 mL of toluene was added. N-BuLi (251.16 mL, 1.6 M, 402 mmols) was added slowly to the toluene solution of iPr$_2$NH through a dropping funnel over 70 min. The temperature of the solution increased from 25° C. to 43° C. The mixture was stirred for another 0.5 hour to complete the formation of iPr$_2$NLi. Deprotonation: 1-C$_6$F$_5$CH$_2$Indene (119.086 g, 402 mmols) was weighed into a 2 L round bottomed flask and 300 mL of toluene was added. The iPr$_2$NLi solution made in the previous step was poured into the 1-C$_6$F$_5$CH$_2$Indene solution while monitoring the temperature. The temperature of the reaction mixture reached 40.7° C. following the addition of LDA and the mixture was stirred for another 1.5 hours. A slurry formed due to the formation of solid 1-C$_6$F$_5$CH$_2$IndLi. $^{19}$F NMR (with THF-d$_8$ as solvent) indicated that the reaction was complete. This reaction mixture was used directly in the next step. Metallation: tBu$_3$PNTiCl$_3$ (148.912 g, 402 mmol), prepared as above in Inventive Example 3, was pre-weighed and transferred to a 3 L round bottomed flask. Toluene (500 mL) was added to make a slurry. The 1-C$_6$F$_5$CH$_2$IndLi solution from the last step was added through a cannula to the t-Bu$_3$PNTiCl$_3$ slurry over 10 minutes. The color of the reaction became bright orange. The temperature of the reaction mixture reached 40.7° C. after the addition of the indenide salt. The reaction mixture was then stirred overnight, and then left to stand without stirring for 3 hours. Next, the supernatant, which contained some suspended LiCl was decanted off. The remaining yellow solid was dissolved in about 500 mL of dichloromethane. This solution was filtered through at least 2 inches of compact celite on a glass filter frit and the celite was rinsed several times with dichloromethane. The filtrate was pumped to dryness yielding the product (1-C$_6$F$_5$CH$_2$Ind)(t-Bu$_3$P=N)TiCl$_2$ as crystalline solid. The product solid was washed with pentane (3×100 mL) and dried to 250 mTorr to give pure (1-C$_6$F$_5$CH$_2$Ind)(t-Bu$_3$P=N)TiCl$_2$. The weight of the solid was 256.50 g. Meanwhile, the supernatant (with suspended with LiCl) was filtered through at least 2 inches of compact celite on a glass filter frit and the celite was thoroughly rinsed with toluene. The filtrate was pumped to about 20 mL and the product precipitated out of solution. The suspension was filtered and the solid retained was rinsed with toluene (2×20 mL), pentane (2×20 mL) and dried under vacuum. The solid product weighed 11 g. The combined yield was 256.50 g+11 g=257.5 g of (1-C$_6$F$_5$CH$_2$Ind)(t-Bu$_3$P=N)TiCl$_2$, 92% yield and the product was pure. $^{19}$F NMR, δ(THF-d$_8$): 145.6 (m, 2F), 160.0 (m, 1F), 166.4 (m, 2F). $^{31}$P NMR, δ(THF-d$_8$): 46.0 (s). $^1$H NMR, δ(THF-d$_8$): 7.69 (m, 1H), 7.48 (m, 1H), 7.1-7.25 (m, 2H), 6.91 (m, 1H), 6.52 (m, 1H), 4.57 (d, J=14 Hz, 1H), 4.20 (d, J=14 Hz), 2.31 (s, 3H), 1.58 (d, J=14 Hz, 27H).

A person skilled in the art will recognize that the below reaction sequence can be carried out at moderate temperatures, in a single solvent and at large scale (at least 400 mmol) to provide the desired product in high overall yield and purity.

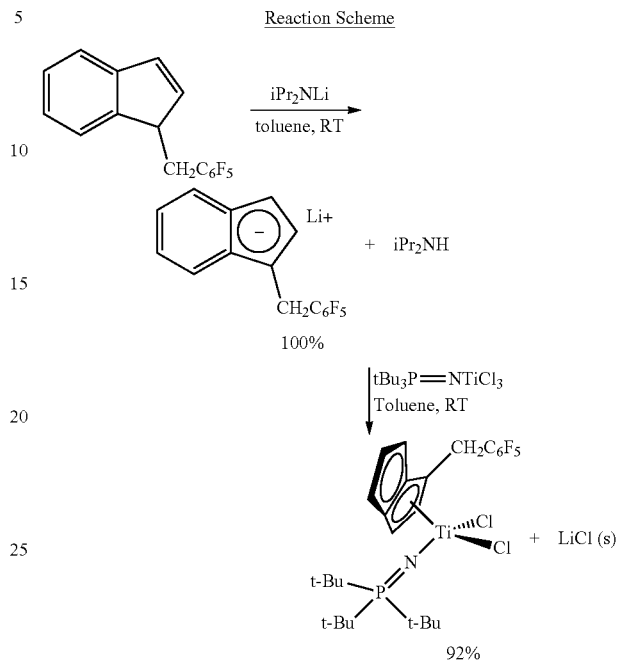

Reaction Scheme

The present invention has been described with reference to certain details of particular embodiments thereof. It is not intended that such details be regarded as limitations upon the scope of the invention except insofar as and to the extent that they are included in the accompanying claims.

What is claimed is:

1. A method for making R$^1_3$P=N—TiCl$_3$, said method comprising combining TiCl$_3$(OR) with an approximately equimolar amount of R$^1_3$P=N—SiMe$_3$ in the presence of a solvent, to give as reaction products the R$^1_3$P=N—TiCl$_3$ and RO—SiMe$_3$ wherein R$^1$ is independently selected from a C$_{1-30}$ hydrocarbyl radical which is unsubstituted or further substituted by one or more halogen atom, a C$_{1-8}$ alkoxy radical, a C$_{6-10}$ aryl radical, a C$_{6-10}$ aryloxy radical, an amido radical, a silyl radical, and a germanyl radical; and wherein R is a primary, secondary or tertiary alkyl group or an aromatic group.

2. The method of claim 1, wherein the TiCl$_3$(OR) is generated by combining TiCl$_4$ with an approximately equimolar amount of ROH.

3. The method of claim 2 wherein the TiCl$_3$(OR) is generated by adding ROH to TiCl$_4$.

4. The method of claim 1, wherein the TiCl$_3$(OR) is generated by combining TiCl$_4$ with Ti(OR)$_4$ in a molar ratio of approximately 3:1.

5. The method of claim 4 wherein the TiCl$_3$(OR) is generated by adding Ti(OR)$_4$ to TiCl$_4$.

6. The method of claim 1 wherein each R$^1$ is a C$_{1-20}$ alkyl radical, a C$_{1-8}$ alkoxy radical, a C$_{6-10}$ aryl radical, a C$_{6-10}$ aryloxy radical, an amido radical, a silyl radical, or a germanyl radical.

7. The method of claim 1 wherein each R$^1$ is a C$_{1-20}$ alkyl radical.

8. The method of claim 1 wherein each R$^1$ is selected from propyl, butyl, pentyl, hexyl and octyl.

9. The method of claim 1 wherein each $R^1$ is a tert-butyl group.

10. The method of claim 1 wherein R is a primary or secondary alkyl group.

11. The method of claim 1 wherein R is a primary alkyl group.

12. The method of claim 1 wherein R is methyl, ethyl, propyl, butyl, or pentyl.

13. The method of claim 1 wherein R is methyl, ethyl, n-propyl, n-butyl, iso-propyl, sec-butyl, or neo-pentyl.

14. The method of claim 1 wherein R is methyl, ethyl or iso-propyl.

15. The method of claim 1 wherein R is methyl.

16. The method of claim 1 wherein R is ethyl.

17. The method of claim 1 wherein R is isopropyl.

18. The method of claim 1, wherein the solvent is a hydrocarbon solvent.

19. The method of claim 1, wherein the solvent is a hydrocarbon solvent and the $R^1_3P=N-SiMe_3$ is added to the $TiCl_3(OR)$.

20. A method for making $(1-R^2-Indenyl)Ti(N=PR^1_3)Cl_2$ comprising the following steps:
   i) combining $TiCl_3(OR)$ with an approximately equimolar amount of $R^1_3P=N-SiMe_3$ to give $R^1_3P=N-TiCl_3$;
   ii) combining a 1-substituted indene $1-R^2-C_9H_7$ with an approximately equimolar amount of lithium di-isopropylamide to give a 1-substituted indenide $1-R^2-C_9H_6$ anion;
   iii) combining the 1-substituted indenide $1-R^2-C_9H_6$ anion with the $R^1_3P=N-TiCl_3$ to give $(1-R^2-Indenyl)Ti(N=PR^1_3)Cl_2$; wherein
   $R^1$ is independently selected from a $C_{1-30}$ hydrocarbyl radical which is unsubstituted or further substituted by one or more halogen atom, a $C_{1-8}$ alkoxy radical, a $C_{6-10}$ aryl radical, a $C_{6-10}$ aryloxy radical, an amido radical, a silyl radical, and a germanyl radical; R is a primary, secondary or tertiary alkyl group or an aromatic group; and $R^2$ is a substituted or unsubstituted alkyl group, a substituted or unsubstituted aryl group, or a substituted or an unsubstituted benzyl group.

21. The method of claim 20 wherein each $R^1$ is a $C_{1-20}$ alkyl radical, a $C_{1-8}$ alkoxy radical, a $C_{6-10}$ aryl radical, a $C_{6-10}$ aryloxy radical, an amido radical, a silyl radical, or a germanyl radical.

22. The method of claim 20 wherein each $R^1$ is a $C_{1-20}$ alkyl radical.

23. The method of claim 20 wherein each $R^1$ is selected from propyl, butyl, pentyl, hexyl and octyl.

24. The method of claim 20 wherein each $R^1$ is tertiary butyl group (t-Bu).

25. The method of claim 20 wherein $R^2$ is an alkyl group, an aryl group, or a benzyl group, wherein each alkyl, aryl and benzyl are optionally further substituted with groups selected from alkyl groups, aryl groups, alkoxy groups, aryloxy groups, alkylaryl groups, arylalkyl groups and halide groups.

26. The method of claim 20 wherein $R^2$ is a benzyl group which is unsubstituted or substituted with at least one fluoride atom.

27. The method of claim 20 wherein $R^2$ is a pentafluorobenzyl group $(C_6F_5CH_2-)$.

28. The method of claim 20 wherein R is a primary alkyl group or a secondary alkyl group.

29. The method of claim 20 wherein R is a primary alkyl group.

30. The method of claim 20 wherein R is methyl, ethyl, propyl, butyl, or pentyl.

31. The method of claim 20 wherein R is methyl, ethyl, n-propyl, n-butyl, iso-propyl, sec-butyl, or neo-pentyl.

32. The method of claim 20 wherein R is methyl, ethyl or iso-propyl.

33. The method of claim 20 wherein R is methyl.

34. The method of claim 20 wherein R is ethyl.

35. The method of claim 20 wherein R is isopropyl.

* * * * *